United States Patent [19]

Okada et al.

[11] Patent Number: 5,698,611
[45] Date of Patent: Dec. 16, 1997

[54] DENTURE BASE RELINING RESINS

[75] Inventors: Junichi Okada; Hirohisa Tsukamoto, both of Tokyo, Japan

[73] Assignee: GC Corporation, Tokyo, Japan

[21] Appl. No.: 612,501

[22] Filed: Mar. 7, 1996

[30] Foreign Application Priority Data

Mar. 13, 1995 [JP] Japan .................................. 7-079333

[51] Int. Cl.$^6$ .............................. A61C 13/23; C08K 5/18
[52] U.S. Cl. .......................... 523/120; 524/533; 524/558; 524/248; 522/14; 433/168.1; 523/109; 523/116
[58] Field of Search ........................ 523/116, 120; 524/533, 558, 248; 522/14; 433/168.1

[56] References Cited

U.S. PATENT DOCUMENTS

| | | | |
|---|---|---|---|
| 4,340,532 | 7/1982 | Lee, Jr. et al. | 523/219 |
| 5,306,338 | 4/1994 | Tsunekawa | 523/116 |
| 5,364,890 | 11/1994 | Sakuma et al. | 523/118 |
| 5,436,283 | 7/1995 | Okada et al. | 523/120 |
| 5,500,454 | 3/1996 | Obana et al. | 523/120 |

FOREIGN PATENT DOCUMENTS 0156605  8/1985  Japan ...................................... 523/116

*Primary Examiner*—Andrew E. C. Merriam
*Attorney, Agent, or Firm*—Oblon, Spivak, McClelland, Maier & Neustadt, P.C.

[57] ABSTRACT

The denture base relining resin comprises a powder component that is a methacrylate ester polymer powder with benzoyl peroxide added thereto and a liquid component that comprises a combination of methyl methacrylate, a methacrylate and a monomer having a specific structure with at least one compound selected from 4-dimethylaminobenzoate and 4,4'-dimethylaminobenzophenone, a specific tertiary amine and a polymerization inhibitor, all incorporated in said liquid component at specific ratios.

6 Claims, No Drawings

DENTURE BASE RELINING RESINS

BACKGROUND OF THE INVENTION

This invention relates to a denture base relining resin comprising a powder component and a liquid component, which is used to regulate the fitness of a specific denture base to the morphology of the oral cavity. For use, the powder and liquid components are mixed together. Then, the mixture is cast up on the mucosal side of the denture base for polymerization and curing in conformity to the morphology of the oral cavity.

A denture, when its fitness to the mucosa of the mouth becomes worse, causes pain to the wearer during mastication, and is likely to come off. Such a denture is now regulated in terms of its fitness by use of a dental material called a denture base relining resin. Upon cast up on the surface of the mucosal side of a denture and inserted into the oral cavity, the denture base relining resin flows and cures in conformity to the morphology of the oral mucosa, thereby improving the fitness of the denture.

As described in Hirasawa et al., "Outline of the general aspects and material dynamics of a variety of commercially available rebase materials" (see *Quintessence of the dental technology*, Vol. 12/1987, DECEMBER, p. 1475), methyl methacrylate, and isobutyl methacrylate are used as the main liquid components of conventional denture base relining resins. However, denture base relining resins containing such monomers are very uncomfortable for patients who receive treatment, using such relining resins because they irritate the oral mucosa and have an unpleasant odor.

A denture base relining resin must flow into a slight gap defined between a denture and the oral mucosa for curing. This relining resin must also have a reduced viscosity so that it can be cast up on the denture. However, since the denture base relining resin tends to run down in the oral cavity if its viscosity is kept low over some long period, it must have the property of gaining a rapid increase in viscosity for curing. This property results from the dissolution of a methacrylate polymer of which powder component is the main component of the denture base relining resin in the liquid component. This is the reason methyl methacrylate and isobutyl methacrylate, in which the methacrylate polymer is well soluble, are used for the denture base relining resin in spite of the fact that they irritate the oral mucosa and have an unpleasant odor.

In recent years, some denture base relining resins free from either methyl methacrylate or isobutyl methacrylate have been developed so as to reduce unpleasant odors and irritations to the oral mucosa, and are put on the market in the form of low-irritative relining resins. However, it has turned out that the low-irritative relining resins have a problem in that they are much lower than conventional relining resins containing methyl methacrylate in terms of the ability of their surfaces to be cured. Arima et al., Paper #1-2-9, Extended Abstracts, 91th Meeting of the Japan Prosthodontic Society, disclose that when commercially available low-irritative relining resins are cured in the air, unpolymerized layers as thick as 249 μm and 267 μm are found, and when cured in water, 127 μm and 163 μm are found.

Upon a denture lined with a relining resin containing such a thick unpolymerized layer being used in the mouth over an extended period of time, the mouth is likely to be adversely affected by the dissolution of the monomer. The denture also has some problems due to an unsatisfactory degree of curing of said relining resin, for instance, poor physical properties, a strong likelihood of discoloration, and poor durability. In the same paper as above mentioned, Arima et al. disclose that a certain type of curing promotion treatment is effective for providing a solution to these problems. However, it is clinically difficult for dentists to carry out such treatment because troublesome and time-consuming steps are needed. Thus, a novel denture base relining resin is strongly demanded, which does not only cause little irritations to the oral mucosa but can also be fully cured on the surface without undue treatment.

As mentioned, the denture base relining resin must flow into a slight gap defined between the denture and the oral mucosa for curing. This relining resin must also have a reduced viscosity so that it can be cast up on the denture. However, since the denture base relining resin runs down in the oral cavity if its viscosity is kept low over some long period, it must have the property of gaining a rapid increase in viscosity for curing. A clinically easy-to-use relining resin will be obtained if the liquid and powder components reach a viscosity of 1,500 Pa·sec. within 8 to 15 min., upon mixed together. When a denture base relining resin is designed with this in mind, it is very important that care be taken of the following two points:

First, a methacrylate polymer which is as easily soluble in a monomer as possible is used as the powder component.

Second, a methacrylate in which the polymer powder is soluble as readily as possible is used as the liquid component.

While these points are taken into consideration, a conventional type of denture base relining resin is composed of polyethyl methacrylate for the powder component and methyl methacrylate or isobutyl methacrylate for the liquid component. However, methyl methacrylate and isobutyl methacrylate cause some considerable irritations to the oral mucosa and have an unpleasant odor. To obtain a denture base relining resin which causes little irritations to the oral mucosa and has no unpleasant odor, therefore, it is required not only to satisfy the above-mentioned two points but to choose a methacrylate that causes little irritations to the oral mucosa and has no or little unpleasant odor as well. By use of an alkyl methacrylate with the molecular weight being higher than those of methyl methacrylate or isobutyl methacrylate, it is possible to improve odor, etc., because it has a high boiling point and so is less volatile. However, the monomethacrylate having a high molecular weight is disadvantageous in that its brittle temperature is low. Generally, a polyalkyl methacrylate becomes much lower in brittle temperature than methyl methacrylate as there is an increase in the number of carbons of the alkyl group thereof. Thus, a denture base relining resin in which the main liquid component is a monomethacrylate is soft and so is likely to be scratched. American Dental Association Standard No. 17 is concerned with a denture base relining resin, and prescribes that the Knoop hardness of said relining resin shall be 10 or more. Depending on what ratio the powder and liquid components are mixed at, Knoop hardness may depart from this standard. In general, a high-molecular-weight monomethacrylate, when polymerized at normal temperature using a peroxide and an amine as catalysts, is lower in polymerizability than methyl methacrylate or isobutyl methacrylate.

As disclosed in Japanese Patent Application Laid-Open Nos. 62-178502, 3-74311, 3-206012, 3-206013, 4-29911, 6-48912, and 6-56619, on the other hand, it has been proposed to replace low-irritative monomers having no unpleasant odor for methyl methacrylate or isobutyl methacrylate. However, compositions obtained by the polymerization of such monomers at normal temperature using a peroxide and an amine as catalysts are all poor in the ability of their surface layers to be cured, so that thick unpolymerized layers remain not only on the surfaces coming into contact with the air but also on the portions cured while brought into close contact with the oral mucosa. For this reason, no sufficient durability is achieved without recourse to some curing promoter.

An object of this invention is to eliminate the above-mentioned problems by the provision of a denture base relining resin which causes no irritations to the oral mucosa and has no unpleasant odor, and enables its surface layer to be highly polymerized without use of any special curing promoter as well.

SUMMARY OF THE INVENTION

According to the present invention, the above-mentioned object is achieved by the provision of a denture base relining resin the polymerization of which is initiated by mixing powder and liquid components, wherein:

said powder component is a methacrylate polymer powder with benzoyl peroxide added thereto, and said liquid component comprises:

(a) 2.5 to 15.0% by weight of methyl methacrylate, (b) 20 to 40% by weight of one or more members selected from compounds having the following structural formula (1):

Formula (1)

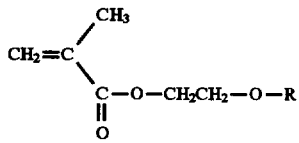

wherein R represents an alkyl or phenyl group, (c) 41 to 75% by weight of one or more methacrylates having two or three methacryloyl group per molecule, (d) 0.5 to 1.5% by weight of at least one member selected from 4-dimethylaminobenzoate and 4,4'-dimethylaminobenzophenone, (e) 2.0 to 3.0% by weight of an aromatic tertiary amine other than 4-dimethylaminobenzoate and 4,4'-dimethylaminobenzophenone, and (f) 0.09 to 0.15% by weight of a polymerization inhibitor.

According to the present invention, it has been found that this denture base relining resin causes little irritations to the oral mucosa and has no unpleasant odor. In addition, an unpolymerized surface layer, if any, can be reduced without recourse to any extra treatment.

Preferably, the compound having formula (1) is n-butoxyethyl methacrylate.

Preferably, the methacrylate having two or three methacryloyl groups per molecule is 1,6-hexanediol dimethacrylate and/or neopentyl glycol dimethacrylate.

Preferably, the aromatic tertiary amine other than 4-dimethylaminobenzoate and 4,4'-dimethylaminobenzophenone is one or more members selected from the group consisting of dipropanol p-toluidine, p-tolyldiethanolamine, and dimethyl p-toluidine.

ILLUSTRATIVE EXPLANATION OF THE INVENTION

The denture base relining resin according to the present invention will now be explained at great length.

In the present invention, the methacrylate polymer is used for the main ingredient of the powder component. It is preferable to use polyethyl methacrylate powders as is the case with a conventional type of denture base relining resin. Polymethyl methacrylate powders cannot be used for the present invention because they show a sufficient solubility only in high-irritative monomers, e.g., methyl methacrylate. Other polymer powders readily soluble in plasticizers, as exemplified in Japanese Patent Application Laid-Open No. 6-279224, may also be used. These powders, because of being well soluble in a high-molecular-weight monomethacrylate, may be used for a low-irritative denture base relining resin. In some cases, however, they remain sticky even upon mixed with the liquid component to thereby increase the viscosity of the denture base relining resin. Since the denture base relining resin of the present invention is polymerized at normal temperature, it is required to add benzoyl peroxide to the powder component as a catalyst. Usually, it is convenient to use a normal-temperature polymerization type of denture base relining resin the curing of which is completed within a period of 8 to 15 minutes. In the denture base relining resin of the present invention, therefore, 0.5 to 1.5% by weight of benzoyl peroxide is added to the powder component.

In the present invention, strict limitation must be imposed on the type and amount of the compound in each ingredient contained in the liquid component. Otherwise, it is impossible to obtain a denture base relining resin which causes little irritations to the oral mucosa and has no unpleasant odor, and is excellent in the ability of the surface to be cured as well.

To be more specific, the liquid component of the denture base relining resin according to the present invention contains 20 to 40% by weight of one or more members selected from the group comprising compounds represented by the following structural formula (1).

Formula (1)

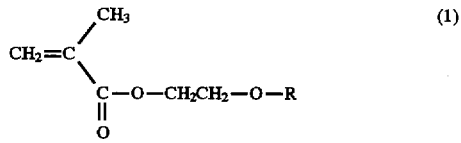

wherein R represents an alkyl or phenyl group. The alkyl group, if it has less than 3 or more than 4 carbon atoms, is not preferable because the irritations of the monomer tend to manifest themselves in the former case and, in the latter case, the hardness of the denture base relining resin tend to drop upon cured or the solubility of the polymer therein tend to decrease. For this reason, when R represents an alkyl group, that alkyl group has preferably 3 or 4 carbon atoms. Compounds containing a phenyl group, too, are preferably used; however, care must be taken of their use, because the transparency of the cured product is unfavorably affected due to its index of refraction higher than that of polyethyl methacrylate. Several illustrative structures represented by R are given below. For the above-mentioned reasons, however, it is desirable to use n-butoxyethyl methacrylate.

Formura (4)

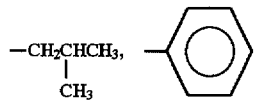

The solubility of the polymer in said compounds having formula (1) is high. However, unless said compound having formula (1) is contained in the liquid component of the denture base relining resin according to the present invention in an amount of at least 20% by weight, it is not possible to achieve any rapid increase in the viscosity of the denture base relining resin upon the powder and liquid components mixed together. However, it is to be noted that the amount of said compound having formula (1) should not exceed 40% by weight, because there is then a drop in the Knoop hardness of the cured product. In other words, the more the amount of said compound having formula (1) is used, the rapider the viscosity increase will be upon mixed, but the more likely the cured product will be scratched. If the particle size of the polymer is half or less than that used for the conventional denture base relining resins, it may then be possible to make the viscosity increase upon mixed rapid while the amount of the above-mentioned compound having formula (1) is kept at 40% or less by weight. However, it is desired that the polymer particle size is not excessively fine, because air bubbles are likely to be formed during mixing, ending up in physical degradation of the cured product. It is thus usually desired that the average particle size of the polymer be between 30 µm and 100 µm.

The incorporation of methyl methacrylate in the liquid component, too, is very important to permit the denture base relining resin according to the present invention to have the desired properties. That is, it is essentially required to incorporate 2.5 to 15.0% by weight of methyl methacrylate in the liquid component so as to obtain the denture base relining resin that increases rapidly in viscosity, has a high surface hardness, and contains lesser air bubbles. Even at as small amount as 2.5% by weight of methyl methacrylate, the denture base relining resin can have an improved surface polymerizability, and allows the liquid component to be well mixed with the powder component upon mixed, thus making it possible to reduce air bubbles contained in the cured product. Methyl methacrylate is an irritating and malodorous ingredient but, at 15.0% or less by weight, it is almost free from irritations to the oral mucosa and has no substantial unpleasant odor.

For the third ingredient of the liquid component of the denture base relining resin according to the present invention, the methacrylate monomer having 2 or 3 methacryloyl groups per molecule is used. This monomer is used for the purpose of promoting the curing of the denture base relining resin, although its ability to solubilize the polymer powder is low. Preferable for this purpose is a monomer that has a low viscosity and does not have any special functional group causing irritations to the oral mucosa, as exemplified by 1,3-butanediol dimethacrylate, 1,4-butanediol dimethacrylate, 1,6-hexanediol dimethacrylate, neopentyl glyclol dimethacrylate, trimethylolpropane trimethacrylate and bis(2-methacryloxypolyethoxyphenyl)propane etc., among which 1,6-hexanediol dimethacrylate, and neopentyl glycol dimethacrylate are most preferable because they cause little irritations to the oral mucosa while they allow the polymer powder to be more or less dissolved therein. Care must be taken of the use of some compounds such as bis(2-methacryloxyethyl)-2,2,4-trimethylhexamethylene dicarbamate, and bisphenol-A diglycidyl methacrylate etc., because they are very viscous and likely to entrain air bubbles upon mixed with the powder component. Said third monomer ingredient is incorporated in the denture base relining resin in an amount of 41 to 75% by weight. In case of the amount is under 41% by weight, it is less effective for promoting the curing of the denture base relining resin whereas, in case of the amount is over 75% by weight, its ability to solubilize the polymer powder tends to drop. It is here to be understood that ethylene glycol dimethacrylate and triethylene glycol dimethacrylate may also be used. However, it is desired that the amount of said two monomers, when used, is limited to 10% or less by weight because of their bitter taste.

At least one member selected from the group comprising compounds 4-dimethylaminobenzoate and 4,4'-dimethylaminobenzophenone should be incorporated in the liquid component of the denture base relining resin according to the present invention in an amount of 0.5 to 1.5% by weight. Said compounds are usually used for the photopolymerization of a methacrylate monomer in combination with a photopolymerization catalyst. According to the present invention, it has now been found that by the incorporation of 0.5 to 1.5% by weight of said compounds together with 0.09 to 0.15% by weight of the polymerization inhibitor (to be described later) in the liquid component makes it possible to improve the surface curing property of a normal-temperature polymerization type of denture base relining resin. Especially when the denture base relining resin is polymerized in the mouth while it is brought into close contact with the oral mucosa, any undesirable unpolymerized layer is hardly found. It is here to be understood that said compounds, which belong to an aromatic tertiary amine, cannot be used in combination with benzoyl peroxide to polymerize the methacrylate monomer at normal temperature. Examples of 4-dimethylaminobenzoate are ethyl 4-dimethylaminobenzoate, (n-butoxy) ethyl 4-dimethylaminobenzoate, isoamyl 4-dimethylaminobenzoate, and 2-ethylhexyl 4-dimethylaminobenzoate. Aliphatic tertiary amines are also found to be effective for this purpose. However, aliphatic tertiary amines are unsuitable for the present invention because they are of high toxicity and so soluble in water that the cured product can increase in terms of water absorption.

One of the characteristic feature of the denture base relining resin according to the present invention is to incorporate the polymerization inhibitor in the liquid component in an amount larger than usual. The polymerization inhibitor used in the present invention may be the same as used for improving the storage stability of ordinary monomers. For instance, butylhydroxytoluene, 2,4-dimethyl-6-tertiary butylphenol, and p-methoxyphenol etc. may be mentioned. Usually, these compounds are added as polymerization inhibitors to monomers in an amount of 0.01 to 0.02% by weight. In the denture base relining resin according to the present invention, however, it is necessary to use the polymerization inhibitor in an amount considerably larger than usual, i.e., in an amount of 0.09 to 0.15% by weight, because it is used in combination with the compound ingredient such as 4-dimethylaminobenzoate and/or 4,4'-dimethylaminobenzophenone etc. to improve the surface curing property of the denture base relining resin.

The aromatic tertiary amine other than 4-dimethylaminobenzoate and 4,4'-dimethylaminobenzophenone is an essential component to enable the denture base relining resin to be polymerized at normal temperature. Usually, the setting time of a normal-temperature polymerization type of resin is controlled by varying the amount of the aromatic tertiary amine added while the amount of benzoyl peroxide is kept constant. In the case of the denture base relining resin according to the present invention, however, the aromatic tertiary amine other than 4-dimethylaminobenzoate and 4,4'-dimethylaminobenzophenone is added at least 2.0% by weight to eliminate undesirable unpolymerized layer on the surface of the cured material. In case of the amount is over 3.0% by weight, however, the setting time tends to become too fast. In the denture base relining resin of the present invention, it is preferable that the setting time is 8 to 15 minutes at 23° C. For the aromatic tertiary amine other than 4-dimethylaminobenzoate and 4,4'-dimethylaminobenzophenone, any desired amine compound may be used provided that it can produce effect when used in combination with benzoyl peroxide. Of this point, however, care should be taken because there is a curing property variation depending on the type of the aromatic tertiary amine used. Exemplary amines are dipropanol p-toluidine, p-tolyldiethanolamine, and dimethyl p-toluidine etc., which are used alone or in combination thereof. It is here to be noted that dimethyl p-toluidine may improve the ability of the denture base relining resin to be cured on the surface but, in some cases, gives offense to a patient due to an increase in the temperature of heat generated during curing; that is, it is preferable that dimethyl p-toluidine, if used, is used in an amount of 1.5% or less by weight while it is combined with other aromatic tertiary amine. Dipropanol p-toluidine, and p-tolyldiethanolamine are more preferable because they generate heat at a lower temperature and is high in terms of its ability to cure the surface of the denture base relining resin as well.

EXAMPLES

The present invention will now be explained in further detail with reference to the following examples.

In the examples, benzoyl peroxide, dimethyl p-toluidine (hereinafter DMPT for short) and p-tolyldiethanolamine were used as catalysts while butylhydroxytoluene (BHT for short) and hydroquinone monomethyl ether (MEHQ for short) were used as polymerization inhibitors. However, the present invention is in no sense limited to these catalysts and inhibitors.

In the following illustrative and comparative examples, the denture base relining resins were regulated such that the setting time was 8 to 11 minutes at 23° C. for the purpose of comparison. The setting time at 23° C. was measured as follows.

Measurement of Setting Time

Each denture base relining resin sample (1.5 to 1.6 g) was mixed at 23° C. and poured in a rubber cup. Immediately following this, a thermistor thermometer was inserted into the rubber cup to measure the length of time from the beginning of mixing until the temperature of heat generated due to polymerization reached a maximum.

Example 1

Powder Component

Benzoyl peroxide (1.0% by weight) was added to polyethyl methacrylate having an average molecular weight of 500,000 and an average particle size of 60 μm.

| Liquid Component | |
|---|---|
| | % by weight |
| Methyl methacrylate | 15 |
| n-Butoxyethyl methacrylate | 30 |
| 1,6-Hexanediol dimethacrylate | 51.89 |
| Ethyl 4-dimethylaminobenzoate | 1 |
| DMPT | 2 |
| BHT | 0.11 |

A denture base relining resin sample having the above-mentioned composition was prepared and mixed at a powder/liquid ratio of 1.6/1.0 for testing purposes. The results of evaluation testing are reported in Table 1.

It was found that, upon cured, the sample gives out little odor and causes little irritations to the oral mucosa, and contains a very thin unpolymerized layer, both in the air and in the mouth. It was also found that the powder and liquid components are well mixed with each other while air bubbles contained in the sample are decreased.

Example 2

Powder Component

Benzoyl peroxide (1.0% by weight) was added to polyethyl methacrylate having an average molecular weight of 500,000 and an average particle size of 40 μm.

| Liquid Component | |
|---|---|
| | % by weight |
| Methyl methacrylate | 10 |
| n-Butoxyethyl methacrylate | 30 |
| 1,6-Hexanediol dimethacrylate | 56.89 |
| Methyl 4-dimethylaminobenzoate | 1 |
| DMPT | 1 |
| p-Tolyl diethanolamine | 1 |
| BHT | 0.11 |

A denture base relining resin sample having the above-mentioned composition was prepared and mixed at a powder/liquid ratio of 1.6/1.0 for testing purposes. The results of evaluation testing are reported in Table 1.

It was found that, upon cured, the sample gives out little odor and causes little irritations to the oral mucosa, and contains a very thin unpolymerized layer, both in the air and in the mouth. It was also found that the powder and liquid components are well mixed with each other while air bubbles contained in the sample are decreased.

Example 3

Powder Component

Benzoyl peroxide (1.0% by weight) was added to polyethyl methacrylate having an average molecular weight of 500,000 and an average particle size of 40 μm.

| Liquid Component | |
|---|---|
| | % by weight |
| Methyl methacrylate | 10 |
| n-Butoxyethyl methacrylate | 30 |
| 1,6-Hexanediol dimethacrylate | 56.89 |
| Methyl 4-dimethylaminobenzoate | 1 |

-continued

| Liquid Component | % by weight |
|---|---|
| DMPT | 1 |
| Dipropanol p-toluidine | 1 |
| BHT | 0.11 |

A denture base relining resin sample having the above-mentioned composition was prepared and mixed at a powder/liquid ratio of 1.6/1.0 for testing purposes. The results of evaluation testing are reported in Table 1.

It was found that, upon cured, the sample gives out little odor and causes little irritations to the oral mucosa, and contains a very thin unpolymerized layer, both in the air and in the mouth. It was also found that the powder and liquid components are well mixed with each other while air bubbles contained in the sample are decreased.

Example 4

Powder Component

Benzoyl peroxide (1.0% by weight) was added to polyethyl methacrylate having an average molecular weight of 250,000 and an average particle size of 40 µm.

| Liquid Component | % by weight |
|---|---|
| Methyl methacrylate | 3 |
| n-Butoxyethyl methacrylate | 30 |
| 1,6-Hexanediol dimethacrylate | 63.89 |
| 4,4-Dimethylaminobenzophenone | 1 |
| p-Tolyldiethanolamine | 2 |
| BHT | 0.11 |

A denture base relining resin sample having the above-mentioned composition was prepared and mixed at a powder/liquid ratio of 1.6/1.0 for testing purposes. The results of evaluation testing are reported in Table 1.

It was found that, upon cured, the sample gives out little odor and causes little irritations to the oral mucosa, and contains a very thin unpolymerized layer, both in the air and in the mouth. It was also found that the powder and liquid components are well mixed with each other while air bubbles contained in the sample are decreased.

Example 5

Powder Component

Benzoyl peroxide (1.0% by weight) was added to polyethyl methacrylate having an average molecular weight of 250,000 and an average particle size of 40 µm.

| Liquid Component | % by weight |
|---|---|
| Methyl methacrylate | 10 |
| n-Butoxyethyl methacrylate | 25 |
| 1,6-Hexanediol dimethacrylate | 41.4 |
| 1,3-Butanediol dimethacrylate | 20 |
| Methyl 4-dimethylaminobenzoate | 1.5 |
| p-Tolyldiethanolamine | 2 |
| BHT | 0.1 |

A denture base relining resin sample having the above-mentioned composition was prepared and mixed at a powder/liquid ratio of 1.6/1.0 for testing purposes. The results of evaluation testing are reported in Table 1.

It was found that, upon cured, the sample gives out little odor and causes little irritations to the oral mucosa, and contains a very thin unpolymerized layer, both in the air and in the mouth. It was also found that the powder and liquid components are well mixed with each other while air bubbles contained in the sample are decreased.

Example 6

Powder Component

Benzoyl peroxide (1.0% by weight) was added to polyethyl methacrylate having an average molecular weight of 500,000 and an average particle size of 60 µm.

| Liquid Component | % by weight |
|---|---|
| Methyl methacrylate | 15 |
| n-Butoxyethyl methacrylate | 30 |
| 1,6-Hexanediol dimethacrylate | 52.39 |
| Ethyl 4-dimethylaminobenzoate | 0.5 |
| DMPT | 2 |
| BHT | 0.11 |

A denture base relining resin sample having the above-mentioned composition was prepared and mixed at a powder/liquid ratio of 1.5/1.0 for testing purposes. The results of evaluation testing are reported in Table 1.

It was found that, upon cured, the sample gives out little odor and causes little irritations to the oral mucosa, and contains a very thin unpolymerized layer, both in the air and in the mouth. It was also found that the powder and liquid components are well mixed with each other while air bubbles contained in the sample are decreased.

Example 7

Powder Component

Benzoyl peroxide (1.0% by weight) was added to polyethyl methacrylate having an average molecular weight of 500,000 and an average particle size of 60 µm.

| Liquid Component | % by weight |
|---|---|
| Methyl methacrylate | 10 |
| Phenoxyethyl methacrylate | 30 |
| 1,6-Hexanediol dimethacrylate | 57.39 |
| Ethyl 4-dimethylaminobenzoate | 0.5 |
| DMPT | 2 |
| BHT | 0.11 |

A denture base relining resin sample having the above-mentioned composition was prepared and mixed at a powder/liquid ratio of 1.5/1.0 for testing purposes. The results of evaluation testing are reported in Table 1.

It was found that, upon cured, the sample gives out little odor and causes little irritations to the oral mucosa, and contains a very thin unpolymerized layer, both in the air and in the mouth. It was also found that the powder and liquid components are well mixed with each other while air bubbles contained in the sample are decreased.

Comparative Example 1

Powder Component

Benzoyl peroxide (1.0% by weight) was added to polyethyl methacrylate having an average molecular weight of 500,000 and an average particle size of 40 μm.

| Liquid Component | % by weight |
| --- | --- |
| n-Butoxyethyl methacrylate | 40 |
| 1,6-Hexanediol dimethacrylate | 56.89 |
| Methyl 4-dimethylaminobenzoate | 1 |
| DMPT | 1 |
| p-Tolyldiethanolamine | 1 |
| BHT | 0.11 |

A denture base relining resin sample having the above-mentioned composition was prepared and mixed at a powder/liquid ratio of 1.6/1.0 for testing purposes. The results of evaluation testing are reported in Table 1.

It was found that, upon cured, the sample gives out little odor and causes little irritations to the oral mucosa, but contains a thick unpolymerized layer, both in the air and in the mouth. It was also found that the powder and liquid components are less mixed with each other while air bubbles contained in the sample are considerably increased.

Comparative Example 2

Powder Component

Benzoyl peroxide (1.0% by weight) was added to polyethyl methacrylate having an average molecular weight of 500,000 and an average particle size of 40 μm.

| Liquid Component | % by weight |
| --- | --- |
| Methyl methacrylate | 30 |
| n-Butoxyethyl methacrylate | 39.89 |
| 1,6-Hexanediol dimethacrylate | 27 |
| Methyl 4-dimethylaminobenzoate | 1 |
| DMPT | 1 |
| p-Tolyldiethanolamine | 1 |
| BHT | 0.11 |

A denture base relining resin sample having the above-mentioned composition was prepared and mixed at a powder/liquid ratio of 1.6/1.0 for testing purposes. The results of evaluation testing are reported in Table 1.

It was found that, upon cured, the sample contains a very thin unpolymerized layer, both in the air and in the mouth, but emits an unpleasant odor and causes acute irritations to the oral mucosa. It was also found that the powder and liquid components are well mixed with each other while air bubbles contained in the sample are decreased.

Comparative Example 3

Powder Component

Benzoyl peroxide (1.0% by weight) was added to polyethyl methacrylate having an average molecular weight of 500,000 and an average particle size of 40 μm.

| Liquid Component | % by weight |
| --- | --- |
| Methyl methacrylate | 10 |
| n-Butoxyethyl methacrylate | 25 |
| 1,6-Hexanediol dimethacrylate | 62.89 |
| DMPT | 1 |
| p-Tolyldiethanolamine | 1 |
| BHT | 0.11 |

A denture base relining resin sample having the above-mentioned composition was prepared and mixed at a powder/liquid ratio of 1.6/1.0 for testing purposes. The results of evaluation testing are reported in Table 1.

It was found that, upon cured, the sample gives out a little odor and causes little irritations to the oral mucosa, but contains a thick unpolymerized layer, both in the air and in the mouth. It was also found that the powder and liquid components are well mixed with each other while air bubbles contained in the sample are decreased.

Comparative Example 4

Powder Component

Benzoyl peroxide (1.0% by weight) was added to polyethyl methacrylate having an average molecular weight of 500,000 and an average particle size of 40 μm.

| Liquid Component | % by weight |
| --- | --- |
| Methyl methacrylate | 10 |
| n-Butoxyethyl methacrylate | 40 |
| 1,6-Hexanediol dimethacrylate | 46.98 |
| Ethyl 4-dimethylaminobenzoate | 1 |
| DMPT | 1 |
| p-Tolyldiethanolamine | 1 |
| BHT | 0.02 |

A denture base relining resin sample having the above-mentioned composition was prepared and mixed at a powder/liquid ratio of 1.6/1.0 for testing purposes. The results of evaluation testing are reported in Table 1.

It was found that, upon cured, the sample gives out a little odor and causes little irritations to the oral mucosa, and contains a very thin unpolymerized layer, both in the air and in the mouth. However, the sample was cured within as short as 4 minutes, and so could not be used as a denture base relining resin.

Comparative Example 5

Powder Component

Benzoyl peroxide (1.0% by weight) was added to polyethyl methacrylate having an average molecular weight of 500,000 and an average particle size of 40 μm.

| Liquid Component | % by weight |
| --- | --- |
| Methyl methacrylate | 10 |
| n-Butoxyethyl methacrylate | 59.88 |
| 1,6-Hexanediol dimethacrylate | 27 |
| Ethyl 4-dimethylaminobenzoate | 1 |

| Liquid Component | |
|---|---|
| | % by weight |
| DMPT | 1 |
| p-Tolyldiethanolamine | 1 |
| BHT | 0.12 |

A denture base relining resin sample having the above-mentioned composition was prepared and mixed at a powder/liquid ratio of 1.6/1.0 for testing purposes. The results of evaluation testing are reported in Table 1.

It was found that, upon cured, the sample gives out a little odor and causes little irritations to the oral mucosa, and contains a very thin unpolymerized layer in the mouth. However, the sample was likely to be scratched due to its low Knoop hardness of 7.9. It was also found that the powder and liquid components are well mixed with each other while air bubbles contained in the same were decreased.

Comparative Example 6

Powder Component

Benzoyl peroxide (1.0% by weight) was added to polyethyl methacrylate having an average molecular weight of 500,000 and an average particle size of 40 μm.

| Liquid Component | |
|---|---|
| | % by weight |
| n-Butoxyethyl methacrylate | 59.88 |
| 1,6-Hexanediol dimethacrylate | 37 |
| Ethyl 4-dimethylaminobenzoate | 1 |
| DMPT | 1 |
| p-Tolyldiethanolamine | 1 |
| BHT | 0.12 |

A denture base relining resin sample having the above-mentioned composition was prepared and mixed at a powder/liquid ratio of 1.6/1.0 for testing purposes. The results of evaluation testing are reported in Table 1.

It was found that, upon cured, the sample gives out a little odor and causes little irritations to the oral mucosa, and contains a very thin unpolymerized layer in the mouth. However, the sample was likely to be scratched due to its low Knoop hardness of 7.5. It was also found that the powder and liquid components are well mixed with each other while air bubbles contained in the sample were decreased.

Comparative Example 7

Powder Component

Benzoyl peroxide (1.0% by weight) was added to polyethyl methacrylate having an average molecular weight of 500,000 and an average particle size of 40 μm.

| Liquid Component | |
|---|---|
| | % by weight |
| Methacryloxyethyl propionate | 49.38 |
| 1,6-Hexanediol dimethacrylate | 50 |

| Liquid Component | |
|---|---|
| | % by weight |
| DMPT | 0.6 |
| MEHQ | 0.02 |

A denture base relining resin sample having the above-mentioned composition was prepared and mixed at a powder/liquid ratio of 1.6/1.0 for testing purposes. The results of evaluation testing are reported in Table 1.

It was found that, upon cured, the sample gives out a little odor and causes little irritations to the oral mucosa, but contains a thick unpolymerized layer in the mouth. It was also found that the powder and liquid components are difficult to mix with each other while many air bubbles contained in the sample.

Comparative Example 8

Powder Component

Benzoyl peroxide (1.0% by weight) was added to polyethyl methacrylate having an average molecular weight of 500,000 and an average particle size of 40 μm.

| Liquid Component | |
|---|---|
| | % by weight |
| Methacryloxyethyl butylate | 54.18 |
| 1,6-Hexanediol dimethacrylate | 45 |
| p-Tolyldiethanolamine | 0.8 |
| MEHQ | 0.02 |

A denture base relining resin sample having the above-mentioned composition was prepared and mixed at a powder/liquid ratio of 1.6/1.0 for testing purposes. The results of evaluation testing are reported in Table 1.

It was found that, upon cured, the sample gives out a little odor and causes little irritations to the oral mucosa, but contains a thick unpolymerized layer in the mouth. It was also found that the powder and liquid components are difficult to mix with each other while many air bubbles contained in the sample. The Knoop hardness, too, was 10 or less.

Comparative Example 9

Powder Component

Benzoyl peroxide (1.0% by weight) was added to polyethyl methacrylate having an average molecular weight of 500,000 and an average particle size of 40 μm.

| Liquid Component | |
|---|---|
| | % by weight |
| Methoxytriethylene glycol methacrylate | 30 |
| 1,6-Hexanediol dimethacrylate | 34.98 |
| Trimethylolpropane trimethacrylate | 34 |
| DMPT | 1.0 |
| MEHQ | 0.02 |

A denture base relining resin sample having the above-mentioned composition was prepared and mixed at a powder/liquid ratio of 1.6/1.0 for testing purposes. The results of evaluation testing are reported in Table 1.

It was found that, upon cured, the sample gives out a little odor and causes little irritations to the oral mucosa, but contains a thick unpolymerized layer in the mouth. It was also found that the powder and liquid components are difficult to mix with each other while many air bubbles contained in the sample. The Knoop hardness, too, was 10 or less.

Comparative Example 10

Powder Component

Benzoyl peroxide (1.0% by weight) was added to polyethyl methacrylate having an average molecular weight of 500,000 and an average particle size of 40 μm.

| Liquid Component | % by weight |
|---|---|
| Compound having the following structural formula | 30 |

Formula (5)

$$CH_2=C\begin{matrix}CH_3\\ \\C-O-CH_2CH_2-O-(CH_2CH_2)_2-CH_3\\ \parallel \quad\quad\quad\quad\quad\quad\quad\quad\quad\quad | \\ O\quad\quad\quad\quad\quad\quad\quad\quad\quad\quad CH_3\end{matrix}$$

| | |
|---|---|
| 1,6-Hexanediol dimethacrylate | 34.98 |
| Trimethylolpropane trimethacrylate | 34 |
| DMPT | 1.0 |
| MEHQ | 0.02 |

A denture base relining resin sample having the above-mentioned composition was prepared and mixed at a powder/liquid ratio of 1.6/1.0 for testing purposes. The results of evaluation testing are reported in Table 1.

It was found that, upon cured, the sample gives out a little odor and causes little irritations to the oral mucosa, but contains a thick unpolymerized layer in the mouth. It was also found that the powder and liquid components are difficult to mix with each other while many air bubbles contained in the sample. The Knoop hardness, too, was 10 or less.

Comparative Example 11

Powder Component

Benzoyl peroxide (1.0% by weight) was added to polyethyl methacrylate having an average molecular weight of 500,000 and an average particle size of 40 μm.

| Liquid Component | % by weight |
|---|---|
| Bthoxylethyl methacrylate | 30.0 |
| 1,6-Hexanediol dimethacrylate | 69.18 |
| DMPT | 0.8 |
| MEHQ | 0.02 |

A denture base relining resin sample having the above-mentioned composition was prepared and mixed at a powder/liquid ratio of 1.6/1.0 for testing purposes. The results of evaluation testing are reported in Table 1.

It was found that, upon cured, the sample gives out a little odor and causes little irritations to the oral mucosa, but contains a thick unpolymerized layer in the mouth.

Comparative Example 12

Powder Component

Benzoyl peroxide (1.0% by weight) was added to polyethyl methacrylate having an average molecular weight of 500,000 and an average particle size of 40 μm.

| Liquid Component | % by weight |
|---|---|
| Butoxyethyl methacrylate | 20.0 |
| 1,6-Hexanediol dimethacrylate | 79.18 |
| DMPT | 0.8 |
| MEHQ | 0.02 |

A denture base relining resin sample having the above-mentioned composition was prepared and mixed at a powder/liquid ratio of 1.6/1.0 for testing purposes. The results of evaluation testing are reported in Table 1.

It was found that, upon cured, the sample gives out a little odor and causes little irritations to the oral mucosa, but contains a thick unpolymerized layer in the mouth. It was also found that the sample takes as long as 16 minutes to realize dough stage.

TABLE 1

| | Thickness of unpolymerized layer (μm) | | Knoop Hardness (K.H.N.) | Odor | Irritations to the oral mucosa |
|---|---|---|---|---|---|
| | 23° C. in the air | in the mouth | | | |
| Example 1 | 90 | 10 | 11.0 | O | O |
| Example 2 | 95 | 8 | 11.2 | O | O |
| Example 3 | 100 | 15 | 10.8 | O | O |
| Example 4 | 110 | 20 | 10.5 | O | O |
| Example 5 | 102 | 18 | 10.9 | O | O |
| Example 6 | 109 | 28 | 11.4 | O | O |
| Exaple 7 | 111 | 22 | 11.8 | O | O |
| Comparative Example 1 | 155 | 60 | 9.2 | O | O |
| Comparative Example 2 | 89 | 7 | 11.2 | Δ | Δ |
| Comparative Example 3 | 160 | 70 | 10.0 | O | O |
| Comparative Example 4 | 90 | 5 | 9.9 | O | O |
| Comparative Example 5 | 93 | 15 | 7.9 | O | O |
| Comparative Example 6 | 163 | 80 | 7.5 | O | O |
| Comparative Example 7 | 228 | 83 | 10.0 | O | O |
| Comparative Example 8 | 235 | 91 | 9.5 | O | O |
| Comparative Example 9 | 215 | 79 | 9.5 | O | O |
| Comparative Example 10 | 220 | 92 | 9.4 | O | O |
| Comparative Example 11 | 235 | 85 | 10.0 | O | O |
| Comparative Example 12 | 233 | 75 | 11.0 | O | O |

The evaluation tests were done as follows.

Evaluation of Odor and Irritations to The Oral Mucosa

Each denture base relining resin sample was mixed and, in three minutes later, inserted in the mouth of a volunteer. As compared with a commercially available denture base relining resin (GC Rebaron manufactured by GC Co., Ltd.), the irritations to the oral mucosa and odor were evaluated in terms of symbols O (excellent), Δ (equivalent), and X (inferior). "GC Rebaron" is a conventional type of denture base relining resin in which the liquid component contains methyl methacrylate as its main ingredient.

Thickness of Unpolymerized Layer at 23° C. in the Air

Each denture base relining resin sample was mixed, cast into a mold of φ4×8 mm placed on a glass plate, and flattened on the upper surface for polymerization. Fifteen minutes after the beginning of mixing, the length of the cured product including an unpolymerized layer was measured by means of a micrometer. Subsequently, the unpolymerized portion was rubbed off with ethanol to measure the length as above mentioned, thereby determining the thickness of the unpolymerized layer.

Thickness of Unpolymerized Layer in the Mouth

Each denture base relining resin sample was mixed, cast into a mold of φ4×8 mm placed on a glass plate, and flattened on the upper surface for polymerization while it was into close contact with the oral mucosa. Nine minutes after the beginning of mixing, the sample was removed from within the mouth and fifteen minutes after the beginning of mixing, the length of the cured product including an unpolymerized layer was measured by means of a micrometer. Subsequently, the unpolymerized portion was rubbed off with ethanol to measure the length as above mentioned, thereby determining the thickness of the unpolymerized layer.

Knoop Hardness

The Knoop hardness of each denture base relining resin was measured according to ADA (American Dental Association) standard No. 17.

As can be understood from the foregoing, the denture base relining resin according to the present invention causes no or little irritations to the oral mucosa and has no substantially unpleasant odor. In addition, the present relining resin can be polymerized with no substantial formation of any undesirable unpolymerized layer, so that the ability thereof to be manipulated and cured on the surface can be improved, thus enabling the fitness of a denture to be regulated with ease and high precision.

The obtained denture can meet all the requirements of a denture base relining resin; that is, it has sufficient strength and durability even upon used over an extended period of time, and is excellent in resistance to discoloration as well. Thus, the present relining resin is well satisfactory for both patients and dentists, and so makes a great contribution to dentistry.

What is claimed is:

1. A denture base relining resin the polymerization of which is initiated by mixing powder and liquid components, wherein:

said powder component is a methacrylate ester polymer powder with benzoyl peroxide added thereto, and said liquid component comprises, by weight of the liquid component:

(a) 2.5 to 15.0% by weight of methyl methacrylate, (b) 20 to 40% by weight of one or more compounds selected from compounds having the following structural formula (1);

Formula (1)

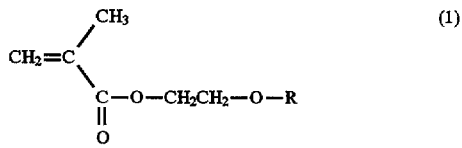

wherein R represents an alkyl or phenyl group, (c) 41 to 75% by weight of one or more methacrylates having two or three methacryloyl groups per molecule, (d) 0.5 to 1.5% by weight of at least one compound selected from ester 4-dimethylaminobenzoate and 4,4'-dimethylaminobenzophenone, (e) 2.0 to 3.0% by weight of an aromatic tertiary amine other than ester 4-dimethylaminobenzoate and 4,4'-dimethylaminobenzophenone, and (f) 0.09 to 0.15% by weight of a polymerization inhibitor.

2. The denture base relining resin as claimed in claim 1, wherein the compound having formula (1) is n-butoxyethyl methacrylate.

3. The denture base relining resin as claimed in claim 1 or 2, wherein the methacrylate ester having two or three methacryloyl groups per molecule is 1,6-hexanediol dimethacrylate and/or neopentyl glycol dimethacrylate.

4. The denture base relining resin as claimed in claim 1, wherein the aromatic tertiary amine other than ester 4-dimethylaminobenzoate and 4,4'-dimethylaminobenzophenone is one or more members selected from the group consisting of dipropanol p-toluidine, p-tolyldiethanolamine, and dimethyl p-toluidine.

5. The denture base relining resin as claimed in claim 2, wherein the aromatic tertiary amine other than ester 4-dimethylaminobenzoate and 4,4'-dimethylaminobenzophenone is one or more members selected from the group consisting of dipropanol p-toluidine, p-tolyldiethanolamine, and dimethyl p-toluidine.

6. The denture base relining resin as claimed in claim 3, wherein the aromatic tertiary amine other than ester 4-dimethylaminobenzoate and 4,4'-dimethylaminobenzophenone is one or more members selected from the group consisting of dipropanol p-toluidine, p-tolyldiethanolamine, and dimethyl p-toluidine.

* * * * *